US00PP32770P2

(12) United States Plant Patent
Grazzini

(10) Patent No.: US PP32,770 P2
(45) Date of Patent: Jan. 26, 2021

(54) ***PHILADELPHUS* PLANT NAMED 'G15097'**

(50) Latin Name: ***Philadelphus* hybrid**
Varietal Denomination: G15097

(71) Applicant: Garden Genetics, LLC, Bellefonte, PA (US)

(72) Inventor: Richard A. Grazzini, Bellefonte, PA (US)

(73) Assignee: GARDEN GENETICS, LLC, Bellefonte, PA (US)

( * ) Notice: Subject to any disclaimer, the term of this patent is extended or adjusted under 35 U.S.C. 154(b) by 0 days.

(21) Appl. No.: 16/873,746

(22) Filed: Jun. 24, 2020

(51) Int. Cl.
*A01H 6/48* (2018.01)
*A01H 5/00* (2018.01)

(52) U.S. Cl.
USPC ..... Plt./226

(58) Field of Classification Search
USPC ..... Plt./226
See application file for complete search history.

*Primary Examiner* — Annette H Para
(74) *Attorney, Agent, or Firm* — Penny J. Aguirre

(57) ABSTRACT

A new cultivar of *Philadelphus* hybrid plant named, 'G15097', characterized by its compact plant habit, its large fully double flowers that have an intense mockorange fragrance, its reliable re-blooming flowering habit, its tolerance to resistance to leaf pathogens common to *Philadelphus* in central Pennsylvania, its sterile, long-lasting flowers, its dense lateral branching, its flowering on both new wood and prior year's wood, and its ease of propagation year around from softwood stem cuttings.

2 Drawing Sheets

Botanical classification: *Philadelphus* hybrid.
Variety denomination: 'G15097'.

BACKGROUND OF THE INVENTION

The present invention relates to a new and distinct cultivar of *Philadelphus*; an interspecific hybrid in origin and botanically known as *Philadelphus* 'G15097', and will be referred to hereafter by its cultivar name, 'G15097'. 'G15097' is a new cultivar of mockorange, a shrub grown for use as an ornamental landscape plant.

The new cultivar was derived from a controlled breeding program conducted by the Inventor at his nursery in Bellefonte, Pa. The overall purpose of the breeding program is to make selections of *Philadelphus* plants with compact plant habits, dense branching, easily produced, large sterile flowers that are strongly fragrant and re-blooming, cold hardiness to at least U.S.D.A. Zone 5 combined with strong resistance to common *Philadelphus* leaf pathogens, and ease of propagation by unrooted cuttings.

'G15097' arose from a cross made in March of 2011 between an unpatented and unpatented proprietary plant from the Inventor's breeding program of *Philadelphus* x *virginalis*, accession no. G13598, as the female parent and *Philadelphus lewsii* 'Snow Velvet' (not patented) as the male parent. Plants were hand pollinated in a greenhouse using vernalized plants brought into flower in late winter. 'G15097' was selected as a single unique plant on Jun. 3, 2015 from amongst the seedlings derived from the above cross.

Asexual propagation of the new cultivar was first accomplished by softwood stem cuttings by the Inventor in Bellefonte, Pa. in June of 2014. Asexual propagation by softwood and hardwood stem cuttings has determined that the characteristics of this cultivar have been determined to be stable and are reproduced true to type in successive generations.

SUMMARY OF THE INVENTION

The following traits have been repeatedly observed and are determined to be the characteristics of the new cultivar. These attributes in combination distinguish 'G15097' as a unique cultivar of *Philadelphus*.

1. 'G15097' exhibits a compact plant habit; reaching 61 cm in width and 122 cm in height as a 5-year-old plant in the landscape.
2. 'G15097' exhibits large fully double flowers that have an intense mockorange fragrance.
3. 'G15097' exhibits a reliable re-blooming flowering habit.
4. 'G15097' exhibits tolerance to resistance to leaf pathogens common to *Philadelphus* in central Pennsylvania.
5. 'G15097' exhibits sterile, long-lasting flowers.
6. 'G15097' exhibits dense lateral branching.
7. 'G15097' exhibits flowers on both new wood and prior year's wood.
8. 'G15097' exhibits ease of propagation year around from softwood stem cuttings.

The female parent differs from 'G15097' in being taller and wider in size, in having flowers that are smaller and semi-double, and in being more susceptible to leaf pathogens. The male parent differs from 'G15097' in being taller and wider in size, in having semi-double flowers, in having a more open and spreading plant habit with arching branches, and in being more susceptible to leaf pathogens. 'G15097' can also be compared to *Philadelphus lemoinei* cultivar 'Avalanche' (not patented) and *Philadelphus* x *virginalis* 'Minnesota Snowflake' (not patented). 'Avalanche' is similar to 'G15097' in having a compact plant habit. 'Avalanche' differs from 'G15097' in having a rounded and globular plant habit with arching stems, single smaller flowers, flowers produced only on prior year's wood and in being susceptible to leaf pathogens. 'Minnesota Snowflake' is similar to 'G15097' in having large double flowers. 'Minnesota Snowflake' differs from 'G15097' in having a much larger plant size, in lacking a re-blooming habit, and in being susceptible to leaf pathogens.

BRIEF DESCRIPTION OF THE DRAWINGS

The accompanying colored photographs illustrate the overall appearance and distinct characteristics of the new *Philadelphus*. The photographs were taken of a five-year-old plant as grown outdoors in trial garden in Bellefonte, Pa.

The photograph in FIG. 1 provides an overall view of the growth habit of 'G15097' in bloom.

Figure 1:
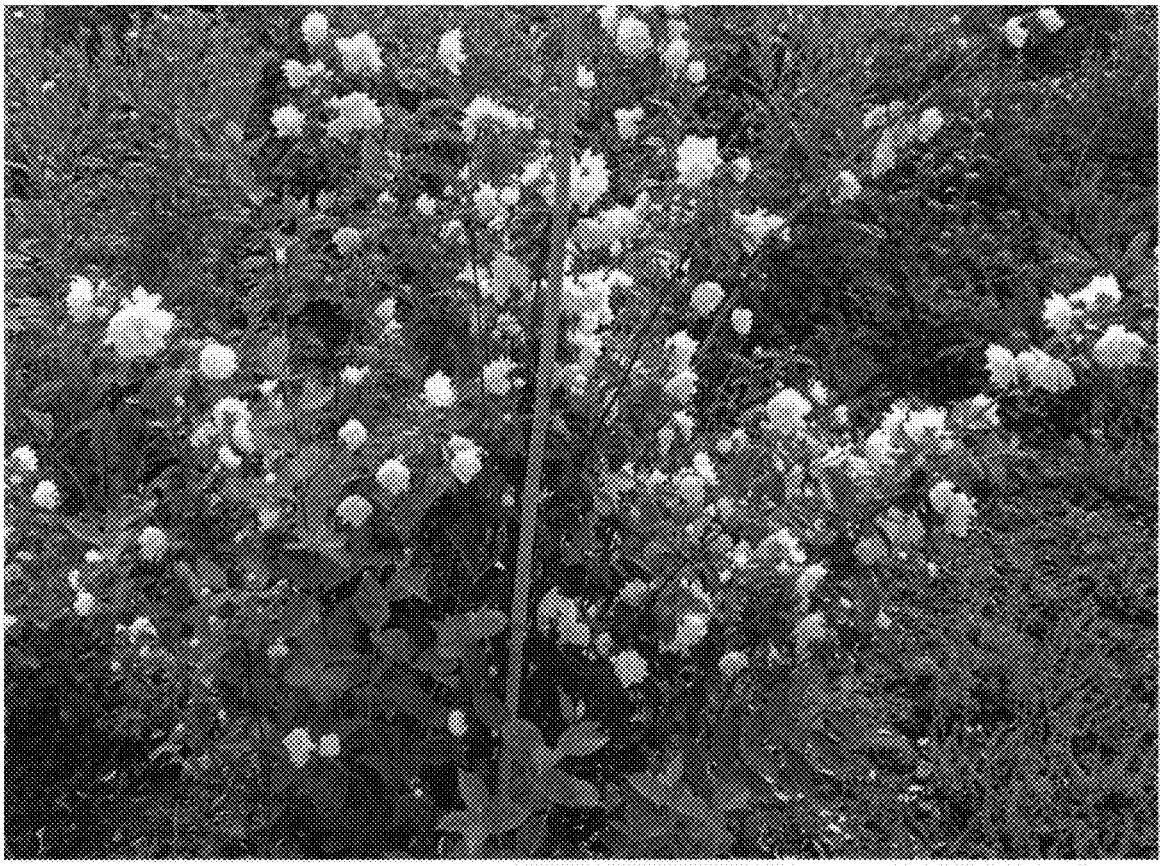
Figure 2:
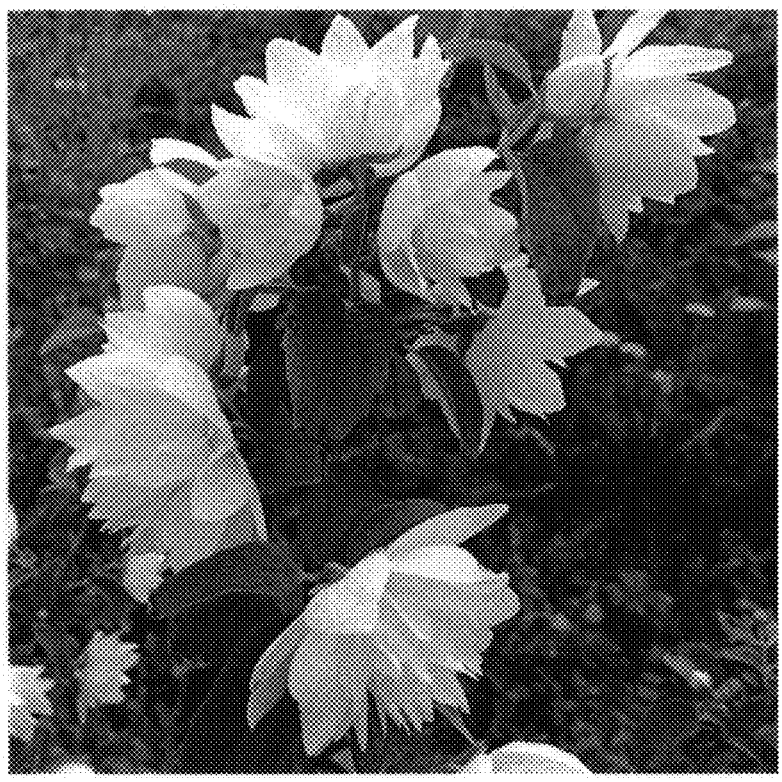

The photograph in FIG. 2 provides a close-up view of numerous flowers of 'G15097'.

Figure 3:
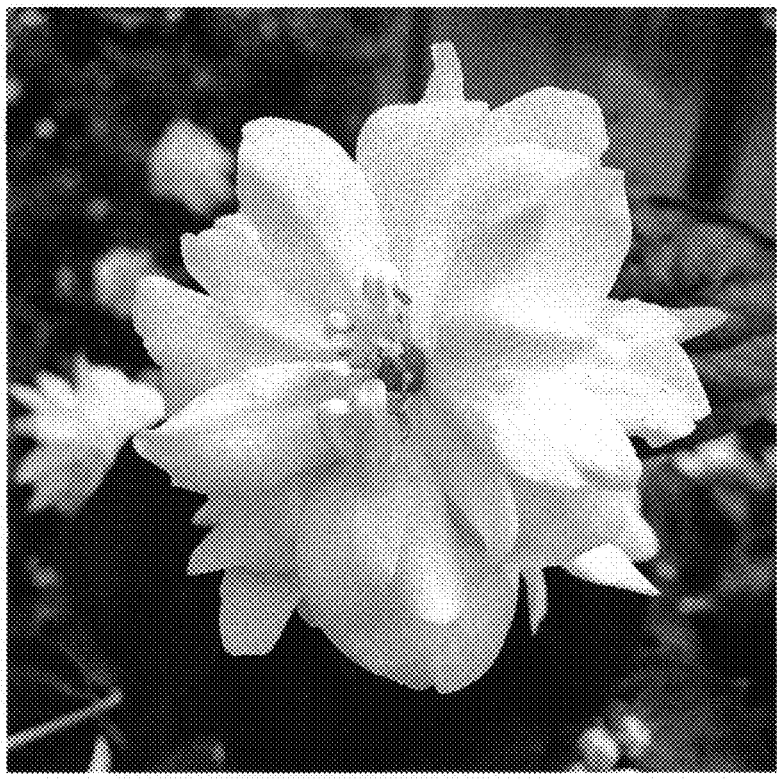

The photograph in FIG. 3 provides a close-up view of a flower of 'G15097'.

The colors in the photographs may differ slightly from the color values cited in the detailed botanical description, which accurately describe the colors of the new *Philadelphus*.

DETAILED BOTANICAL DESCRIPTION

The following is a detailed description of 2-year-old plants (from un-rooted cuttings) of the new cultivar as grown outdoors in 1-gallon containers in Bellefonte, Pa. The phenotype of the new cultivar may vary with variations in environmental, climatic, and cultural conditions, as it has not been tested under all possible environmental conditions. The color determination is in accordance with The 2015 Colour Chart of the Royal Horticultural Society, London, England, except where general color terms of ordinary dictionary significance are used.

General description:

*Blooming period*.—Blooms in late May through mid-June, re-blooming sporadically in summer and fall in Pennsylvania, plants grown in a greenhouse will bloom year around, but bloom is better when a dormant period is given.

*Plant type*.—Deciduous shrub.

*Plant habit*.—Upright.

*Plant size*.—Average of 16 cm in height and 15 cm in width as a plant 2 years in age, reaches an average of 1.22 m in height and 61 cm in width as a 5-year-old plant in the landscape.

*Cold hardiness*.—At least to U.S.D.A. Zone 5.

*Diseases and pests*.—Observed to be tolerant to resistant in field trials to typical *Philadelphus* leaf pathogens including the possible pathogens: bacterial blight; *Pseudomonas syringae* pv. *syringae* and *Pseudomonas syringae* pv. *philadelphi*, grey mold; *Botrytis cinerea*, powdery mildew; *Oidium* cf. *hortensiae*, and *Erysiphe* sp., rust; *Gymnosporangium speciosum*; and fungal leaf spot; *Cercospora angulate*, no susceptibility or resistance to pests has been observed.

*Root description*.—Fibrous, moderately dense, 161C in color.

*Propagation*.—Softwood and hardwood stem cuttings.

*Root development*.—Softwood cuttings initiate roots in 14 to 21 days, rooted cuttings fully develop in a 4-inch container in 90 to 120 days.

*Growth rate*.—Moderate.

Stem description:

*Shape*.—Oval.

*Stem color*.—New growth; N144A, mature wood; a blend of 199B and 198A.

*Stem size*.—Main stem; average of 5 cm in length and 8 mm in diameter, lateral stems; average of 12 cm in length and 3 mm in diameter.

*Stem surface*.—New growth; slightly glossy and very sparsely covered with wooly hairs; average of 0.5 mm in length and match the surface color, mature stems; glabrous and woody, old wood; exfoliating (shreddy), matte.

*Stem aspect*.—Upright to slightly outward.

*Branching*.—Densely branched, 1 main stem, 8 to 12 lateral branches per main stem.

*Internode length*.—An average of 2 cm.

Foliage description:

*Leaf shape*.—Ovate to broadly elliptic.

*Leaf division*.—Simple.

*Leaf base*.—Rounded to slightly cordate.

*Leaf apex*.—Cuspidate.

*Leaf fragrance*.—None.

*Leaf venation*.—Primarily pinnate, upper and lower surface colors match surface colors.

*Leaf margins*.—Serrated.

*Leaf arrangement*.—Opposite.

*Leaf attachment*.—Petiolate.

*Leaf surface*.—Young; upper surface glossy, lower surface matte and very densely covered with wooly pubescence; average of 0.5 mm in length and match leaf color, mature; upper surface slightly glossy, very sparsely covered with short pubescent hairs; 0.5 mm in length, matches leaf surface color, lower surface; slight sheen.

*Leaf size*.—An average of 4.5 cm in length and 3 cm in width.

*Leaf quantity*.—An average of 14 per lateral stem.

*Leaf color*.—Young leaves upper and lower surface; 142A, mature leaves upper surface; 147A, mature lower surface; 147B.

*Petioles*.—About 5 mm in length and 1 mm in width, color 149A, sparsely covered with short soft hairs; 0.5 mm in length match surface color.

Inflorescence description:

*Inflorescence type*.—Solitary axillary fully double flowers.

*Flower buds*.—Globose in shape, an average of 8 mm in depth and 6 mm in diameter, NN155A in color with base matching sepal color.

*Flower fragrance*.—Sweet, citrus-like, strong, typical of mockorange *Philadelphus*.

*Lastingness of flowers*.—Average of 10 to 14 days (less if cross-pollinated), self-cleaning.

*Flower aspect*.—Outward to upright, slightly drooping.

*Flower quantity*.—An average of 2 flowers per lateral stem.

*Flower type*.—Rotate.

*Flower size*.—Up to 3.5 cm in diameter and 5 cm in depth on the plant described, up to 10 cm in height and width on a mature plant.

*Peduncles*.—Average of 1.5 cm in length and 1 mm in diameter, color 144A, oval in shape, moderately strong, surface is matte and very sparsely covered with short pubescent hairs; 0.5 mm in length, match leaf surface color.

*Pedicels*.—None.

*Calyx*.—Rotate in shape with lower portion fused, an average of 5 mm in depth and 1.5 cm in width.

*Sepals*.—4, aristate in shape, acuminate apex, base fused, entire margin, an average of 8 mm in length and 3 mm in width, color on inner and outer surface a blend of 144A and 144C, inner surface is glossy, outer surface is matte, both surfaces are densely pubescent; average of 0.5 mm in length and match surface color.

*Petals*.—Average of 30, un-fused, ranging from orbicular to broadly elliptic to elliptic in shape, margin slightly undulated, apex mucronate to apiculate, up to 3.5 cm in length and 2.5 cm in width, outer and inner surface is glabrous, satiny, with a slight sheen and slightly transparent, color of inner and outer surface when opening and mature; NN155B.

Reproductive organs:

*Gynoecium*.—Pistils; 4, united, average of 1 cm in length, style; average of 9 mm in length, and 155A in color, stigma; 1 mm in length, club-shaped, 1C in color, ovary is inferior and surrounded by nectar secreting disk; 145B in color, 5 mm in diameter and 3 mm in depth.

*Fertility*.—Self-incompatible,

*Androecium*.—None observed.

*Fruit and seed*.—None observed; very minimal seed has been observed if grown with other *Philadelphus*.

It is claimed:

1. A new and distinct cultivar of *Philadelphus* plant named 'G15097' as herein illustrated and described.

* * * * *